United States Patent
Pilgaonkar

(10) Patent No.: US 11,147,767 B2
(45) Date of Patent: Oct. 19, 2021

(54) GASTRORETENTIVE FORMULATIONS

(71) Applicant: RUBICON RESEARCH PRIVATE LIMITED, Thane West (IN)

(72) Inventor: Pratibha Pilgaonkar, Thane West (IN)

(73) Assignee: RUBICON RESEARCH PRIVATE LIMITED, Thane West (IN)

( * ) Notice: Subject to any disclaimer, the term of this patent is extended or adjusted under 35 U.S.C. 154(b) by 0 days.

(21) Appl. No.: 16/800,742

(22) Filed: Feb. 25, 2020

(65) Prior Publication Data

US 2020/0268653 A1 Aug. 27, 2020

(30) Foreign Application Priority Data

Feb. 25, 2019 (IN) .............................. 201921007339

(51) Int. Cl.
| | | |
|---|---|---|
| A61K 9/00 | (2006.01) | |
| A61K 31/198 | (2006.01) | |
| A61K 47/34 | (2017.01) | |
| A61K 47/38 | (2006.01) | |
| A61K 31/41 | (2006.01) | |
| A61K 31/549 | (2006.01) | |

(52) U.S. Cl.
CPC .......... *A61K 9/0065* (2013.01); *A61K 31/198* (2013.01); *A61K 31/41* (2013.01); *A61K 31/549* (2013.01); *A61K 47/34* (2013.01); *A61K 47/38* (2013.01)

(58) Field of Classification Search
CPC .... A61K 9/0065; A61K 31/198; A61K 31/41; A61K 31/549; A61K 47/34; A61K 47/38
See application file for complete search history.

(56) References Cited

U.S. PATENT DOCUMENTS

| | | | |
|---|---|---|---|
| 9,674,585 B2 * | 6/2017 | Kitts | H04N 21/25866 |
| 2010/0233253 A1 * | 9/2010 | Kavimandan | A61K 9/2853 |
| | | | 424/451 |
| 2013/0078290 A1 * | 3/2013 | Pilgaonkar | A61K 9/0065 |
| | | | 424/400 |
| 2015/0231084 A1 * | 8/2015 | Kumar | A61K 9/0004 |
| | | | 424/475 |

OTHER PUBLICATIONS

Sigma-Aldrich entry for "Polyethylene glycol 6000," downloaded Jul. 30, 2020 from https://www.sigmaaldrich.com/catalog/product/mm/807491?lang=en&region=US. (Year: 2020).*
Google patent search_Jul. 29, 2020_vinyl pyrrolidone polyvinyl acetate polymer in controlled release gastroretentive (Year: 2020).*
Google scholar search_Jul. 29, 2020_levodopa gastroretentive "ethyl cellulose" "polyethylene oxide" (Year: 2020).*

* cited by examiner

*Primary Examiner* — Michael P Cohen
(74) *Attorney, Agent, or Firm* — Blank Rome LLP

(57) ABSTRACT

The present invention relates to gastroretentive formulations and to processes for preparation of the same. Particularly, the invention relates to gastroretentive dosage forms comprising at least one swelling agent and at least one swelling retardant.

5 Claims, No Drawings

GASTRORETENTIVE FORMULATIONS

This application claims the benefit of Indian Provisional Application No. 201921007339, filed Feb. 25, 2019, which is incorporated by reference in its entirety.

FIELD OF THE INVENTION

The present invention relates to gastroretentive formulations and to processes for preparation of the same. Particularly, the invention relates to gastroretentive dosage forms comprising at least one swelling agent and at least one swelling retardant.

BACKGROUND OF THE INVENTION

Oral formulations have earned a significant place among the various dosage forms developed. In most of the cases, the conventional oral delivery systems show limited bioavailability because of fast gastric-emptying time among many other reasons involved. Retention of the dosage form in the upper gastrointestinal tract for an extended period of time and release of the drug slowly can address many challenges associated with conventional oral delivery, including poor bioavailability. With gastro-retentive drug delivery systems, gastric retention coupled with drug release for extended time has significantly improved patient compliance. Further to attain required therapeutic activity, recurrent dosing is needed for the drugs with short half-lives as they have the tendency of getting eliminated quickly from the systemic circulation. However, an oral formulation with additional gastric retention property can avoid these limitations by releasing the drug slowly in the upper gastrointestinal tract along with maintaining an effective drug concentration in the systemic circulation for an extended period of time. Benefits of gastro-retentive formulations are thereby many.

Gastro-retentive systems however face issues such as inadequate swelling to cause retention, excessive swelling resulting in rupture of the dosage form. Need continues to exist for improved gastro-retentive systems that swell quickly and adequately to cause gastro-retention and can maintain the swollen structure of the dosage form for prolonged time.

DETAILED DESCRIPTION OF THE INVENTION

The present invention provides improved gastro-retentive formulations. The gastro-retentive formulations of the present invention comprise at least one active agent, at least one swelling agent and at least one swelling retardant. The compositions of the present invention swell voluminously to cause the size of the dosage form to increase such that the swollen dosage form does not pass through the pyloric sphincter resulting in retention of the dosage form for a prolonged period of time. Without being bound to any theory it is believed that the swelling retardant controls the rate of swelling of the dosage form. The swelling agent and the swelling retardant in combination provide gastro-retentive dosage forms that can maintain an adequately swollen structure of the dosage form.

The formulations of the present invention comprise one or more active agents. In one embodiment, the active agents may be of any solubility, permeability or any combinations thereof. In a further embodiment, the active agents may be in the form of an acid, a base, or any salt thereof, prodrugs, active metabolites, polymorphs, solvates, hydrates, enantiomers, optical isomers, tautomers or racemic mixtures thereof. In one embodiment, the formulation of the present invention can be used to deliver different dose ranges of the pharmaceutically active agent. In another embodiment, the formulation of the present invention can be used to deliver high dose pharmaceutically active agent. In a further embodiment, the formulation of the present invention can be used to deliver low dose pharmaceutically active agent. In general all, including, but not limited to, acidic, basic or amphoteric drugs or any combinations thereof can be incorporated in the compositions of the present invention. Non-limiting examples of active agents include anti-diabetic agent, cardiovascular agents, neurological agents, anti-parkinson's disease, anti-infective agents, analgesics, anti-inflammatory agents, anti-arthritic, anti-hyperlipidemic agents, anti-hypertensive, and the like. In another embodiment, the active agents employed in the composition of the present invention include carbidopa, levodopa, valsartan, hydrochlorthiazide, and the like or combinations thereof. In one embodiment the amount of pharmaceutically active agent in the extended release compositions can vary from about 5% by weight to about 85% by weight.

The formulations of the present invention further comprise at least one swelling agent. In one embodiment, the swelling agent employed in the present invention includes, but is not limited to, polyethylene oxide and the like.

In a further embodiment, the formulations of the present invention comprise at least one swelling retardant. In one embodiment, the swelling retardant employed in the present invention includes, but is not limited to, ethyl cellulose and the like The dosage form may further comprise at least one pharmaceutically acceptable excipient, such as, but not limited to, diluents, binders, glidants, lubricants/antiadherent and the like or any combinations thereof. Suitable diluents that may be employed include, but are not limited to, starch, talc, microcrystalline cellulose, lactose, dicalcium phosphate, and the like or any combinations thereof. Suitable binders that may be employed include, but are not limited to, starch, pregelatinized starch, polyvinyl pyrrolidone, copovidone, and the like or any combinations thereof. Suitable lubricants/anti-adherents that may be employed include, but are not limited to, magnesium stearate, calcium stearate, stearic acid, talc, and sodium stearyl fumarate and the like or any combinations thereof. Suitable glidants that may be employed include, but are not limited to, colloidal silicon dioxide, talc, or any combinations thereof.

The compositions of the present invention may optionally comprise one or more release retardants. In one embodiment, the release retardants that may be employed include, but are not limited to, cellulosic polymers, polyvinyl acetate polymers, acrylate and methacrylate polymers and the like or any combinations thereof.

In one embodiment, the formulation of the present invention may be in the form of a monolithic matrix. In a further embodiment, the formulation of the present invention may be in the form of a monolayer. In another embodiment, the formulation of the present invention may be a multi-layered composition. In another embodiment, the dosage form of the present invention may be in the form of a tablet. In another embodiment, the dosage form of the present invention may be coated. In a further embodiment, the dosage form of the present invention may be uncoated.

The term "composition" or "formulation" or "dosage form" or "preparation" has been employed interchangeably for the purpose of the present invention and mean that it is a pharmaceutical formulation which is suitable for administration to a patient. For the purpose of the present invention, the terms "controlled release" or "sustained release" or "extended release" or "modified release" or "prolonged release" have been used interchangeably and mean broadly that the active agent is released at a predetermined rate that is different or slower than immediate release.

In one embodiment, the formulation of the present invention is a gastro-retentive system. In a further embodiment, the formulation of the present invention may be retained in the upper gastrointestinal tract for a period of time of not less than 2 hours. In another embodiment, the swelling index, floating lag time and other relevant parameters are monitored.

The formulations of the present invention are prepared by process such as direct compression, wet granulation, dry granulation and the like or any combinations thereof. The present invention provides process for preparation of the gastro-retentive formulations.

In a further embodiment, based on the active agent employed, the formulations of the present invention can be employed for the treatment of diseases or disorders. The present invention relates to method of treatment of such diseases or disorders.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings without departing from the essential scope thereof. Therefore, it is intended that the invention not be limited to the particular embodiment disclosed, but that the invention will include all embodiments falling within the scope thereof. Details of the present invention, including its objects and advantages, are provided in the non-limiting exemplary illustrations below.

EXAMPLES

Example 1

Atenolol Gastroretentive Tablet

| Ingredients | mg/tablet |
|---|---|
| Atenolol | 50 |
| Ethyl cellulose | 75 |
| Polyethylene oxide | 250 |
| Microcrystalline cellulose | 100 |
| Povidone | 15 |
| Talc | 4.5 |
| Magnesium stearate | 5.5 |
| Total | 500 |

Procedure:

Atenolol, microcrystalline cellulose, part of ethyl cellulose were blended and granulated with povidone. The granules were then blended with remaining ethyl cellulose, polyethylene oxide, and talc and subsequently lubricated with magnesium stearate.

Example 2

Carbidopa-Levodopa Gastroretentive Tablet

| Ingredient | mg/tab |
|---|---|
| Active layer | |
| Carbidopa | 50 |
| Levodopa | 200 |
| Hydroxypropyl methyl cellulose, low viscosity | 30 |
| FD&C Red 40AI. Lake | 0.5 |
| Microcrystalline cellulose | 14.5 |
| Magnesium stearate | 5 |
| Total | 300 |
| Gastroretentive layer | |
| Polyethylene oxide | 80 |
| Hydroxypropyl methyl cellulose, higher viscosity | 80 |
| Crospovidone | 80 |
| Ethyl cellulose | 50 |
| Microcrystalline cellulose | 20 |
| Polyvinyl pyrrolidone | 22 |
| Isopropyl alcohol | qs |
| Water | qs |
| Sodium bicarbonate | 25 |
| Citric acid | 10 |
| Mg. stearate | 3 |
| Total | 370 |
| Total tablet weight | 670 mg |

Procedure: The active layer and gastroretentive layer granulations were made separately and then the two layers were compressed into bi-layered tablets.

Example 3

Valsartan and Hydrochlorthiazide Gastroretentive Tablet

| Ingredient | mg/tab |
|---|---|
| Active layer | |
| Valsartan | 160 |
| Hydroxypropyl methyl cellulose, low viscosity | 30 |
| Microcrystalline cellulose | 50 |
| Magnesium stearate | 5 |
| Total | 245 |
| Gastroretentive layer | |
| Polyethylene oxide | 80 |
| Hydroxypropyl methyl cellulose, higher viscosity | 80 |
| Crospovidone | 80 |
| Ethyl cellulose | 50 |
| Microcrystalline cellulose | 20 |
| Polyvinyl pyrrolidone | 22 |
| Isopropyl alcohol | qs |
| Water | qs |
| Sodium bicarbonate | 25 |
| Citric acid | 10 |
| Mg. stearate | 3 |
| Total | 370 |
| Total tablet weight | 670 mg |

Procedure: The active layer and gastroretentive layer granulations were made separately and then the two layers were compressed into bi-layered tablets. The bi-layered tablet was further coated with a hydroxypropyl methyl cellulose based film coating with 25 mg of hydrochlorthiazide.

I claim:

1. A gastro-retentive bi-layered formulation comprising:
   (a) an active layer comprising at least one active agent, and
   (b) a gastro-retentive layer comprising at least one swelling agent and at least one swelling retardant, wherein the swelling retardant comprises ethyl cellulose.

2. The formulation of claim 1, wherein the active agent is an anti-diabetic agent, a cardiovascular agent, a neurological agent, an anti-Parkinson's disease agent, an anti-infective agent, an analgesic agent, an anti-inflammatory agent, an anti-arthritic agent, an antihyperlipidemic agent, or an antihypertensive agent, or any combination thereof.

3. The formulation of claim 1, wherein the at least one active agent is carbidopa, levodopa or a combination thereof.

4. The formulation of claim 1 wherein the at least one active agent is valsartan, hydrochlorthiazide, or a combination thereof.

5. The formulation of claim 1, wherein the at least one swelling agent comprises polyethylene oxide.

* * * * *